US011819413B2

(12) United States Patent
Hettich et al.

(10) Patent No.: US 11,819,413 B2
(45) Date of Patent: Nov. 21, 2023

(54) MEDICAL CHAIN NET

(71) Applicant: Aesculap AG, Tuttlingen (DE)

(72) Inventors: Georg Hettich, Tuttlingen (DE); Lena Schwanz, Stockach (DE)

(73) Assignee: Aesculap AG, Tuttlingen (DE)

( * ) Notice: Subject to any disclaimer, the term of this patent is extended or adjusted under 35 U.S.C. 154(b) by 0 days.

(21) Appl. No.: 17/297,574

(22) PCT Filed: Nov. 28, 2019

(86) PCT No.: PCT/EP2019/082963
§ 371 (c)(1),
(2) Date: May 27, 2021

(87) PCT Pub. No.: WO2020/109501
PCT Pub. Date: Jun. 4, 2020

(65) Prior Publication Data
US 2022/0015909 A1  Jan. 20, 2022

(30) Foreign Application Priority Data

Nov. 28, 2018 (DE) ..................... 10 2018 130 205.3

(51) Int. Cl.
*A61F 2/28* (2006.01)
*A61F 2/30* (2006.01)

(52) U.S. Cl.
CPC .. *A61F 2/2846* (2013.01); *A61F 2002/30062* (2013.01); *A61F 2002/30276* (2013.01)

(58) Field of Classification Search
CPC .......... A61F 2/2846; A61F 2002/30062; A61F 2002/30276
See application file for complete search history.

(56) References Cited

U.S. PATENT DOCUMENTS

| 4,524,500 | A | 6/1985 | Genetay et al. |
| 10,039,651 | B2 | 8/2018 | Weiss et al. |

(Continued)

FOREIGN PATENT DOCUMENTS

| DE | 102012213246 A1 | 1/2014 |
| DE | 102015226063 A1 | 6/2017 |

(Continued)

OTHER PUBLICATIONS

Written Opinion received in International Application No. PCT/EP2019/082963, dated Feb. 27, 2020, with translation, 11 pages.

(Continued)

*Primary Examiner* — Brian A Dukert
*Assistant Examiner* — Melissa A Hoban
(74) *Attorney, Agent, or Firm* — Christopher A. Rothe; Culhane Meadows PLLC

(57) ABSTRACT

A medical product for use during the treatment of a bone defect, having a plurality of individual elements that are connected to one another such that individual elements adjacent to one another engage in one another/are chained to one another. The individual elements of the chain net are subdivided into main elements and connection elements that are designed differently from the main elements. The main elements and the connection elements form, when chained to one another, a grid structure that is flat in the x-y plane.

12 Claims, 8 Drawing Sheets

(56) References Cited

U.S. PATENT DOCUMENTS

| | | | |
|---|---|---|---|
| 2004/0260396 A1* | 12/2004 | Ferree | A61F 2/442 623/17.12 |
| 2009/0024147 A1* | 1/2009 | Ralph | A61B 17/8085 606/151 |
| 2010/0023057 A1* | 1/2010 | Aeschlimann | A61F 2/30749 606/246 |
| 2018/0256352 A1 | 9/2018 | Nyahay et al. | |
| 2018/0271572 A1 | 9/2018 | Whyne et al. | |
| 2018/0368981 A1 | 12/2018 | Mattes et al. | |
| 2019/0231530 A1 | 8/2019 | Mattes et al. | |

FOREIGN PATENT DOCUMENTS

| | | | | |
|---|---|---|---|---|
| DE | 102016211201 A1 | 12/2017 | | |
| EP | 0089883 A1 | 9/1983 | | |
| RU | 152119 U1 | 5/2015 | | |
| RU | 173377 U1 | 8/2017 | | |
| WO | 2008061759 A1 | 5/2008 | | |
| WO | 2015091518 A1 | 6/2015 | | |
| WO | WO-2017103216 A1 * | 6/2017 | | A61F 2/28 |

OTHER PUBLICATIONS

International Search Report received in International Application No. PCT/EP2019/082963, dated Feb. 27, 2020, with translation, 7 pages.
Search Report received in German Application No. 10 2018 130 205.3 dated Sep. 18, 2019, with translation, 19 pages.
Office Action received in Russian Application No. 2021118514/14 dated Dec. 29, 2021, with translation, 16 pages.
Search Report received in Russian Application No. 2021118514/14 dated Dec. 28, 2021, with translation, 5 pages.

* cited by examiner

MEDICAL CHAIN NET

CROSS-REFERENCE TO RELATED APPLICATIONS

This application is the United States national phase entry of International Application No. PCT/EP2019/082963, filed Nov. 28, 2019, and claims the benefit of priority of German Application No. 10 2018 130 205.3, filed Nov. 28, 2018. The contents of International Application No. PCT/EP2019/082963 and German Application No. 10 2018 130 205.3 are incorporated by reference herein in their entireties.

FIELD

The present disclosure relates to a medical product, preferably in the form of a chain net for use in the treatment, in particular in the filling and/or closure, of a bone defect, having a plurality of individual link elements which are connected to each other in such a way that adjacent individual link elements are interlocked/interlinked.

BACKGROUND

Above a certain size, bone defects on the human skeleton do not heal intrinsically. This means that the defects cannot be healed from within on their own, but require medical care. In recent years, various solutions for the treatment of bone defects have become established. Especially during revisions after total hip or knee arthroplasty (hip or knee replacement), there is often a need to fill cavitary bone defects. In the medical field, revision is understood to be the renewed, usually surgical, treatment after therapy has already been performed. The filling of bone defects is also sometimes necessary in the field of spinal and trauma surgery. However, the filling of cavitary bone defects is often difficult, particularly in osteoporotic and tumor-affected bones.

The term cavitary bone defect and/or bone cavity means a cavity or hollow in a human or animal bone, especially in a human or animal articular bone. Here, the cavity may be the result of bone trauma, bone disease, or surgical intervention/reintervention, in particular revision after total hip or knee arthroplasty.

Various treatment options are known from the prior art. For example, DE 9 2013 226 063 A1 discloses a medical product for use in treating a bone cavity, wherein the product comprises a plurality of interconnected members, each member having a circumferential border and wherein the borders of adjacent members interlock.

In order to fill a bone defect, malleable filling materials that can be adapted to the bone, such as calcium phosphate cements, are often used. Scaffolds are often used to provide a grid structure for bone growth. These scaffolds are preformed and rigid and do not adapt to the bone.

In general, a scaffold (also 'framework') is a bioresorbable stent that degrades gradually over a period of 24 months.

For covering bone defects on the acetabulum, metal meshes are used, which have low flexibility. The acetabulum is a hip joint or pelvic socket and in anatomy forms the osseous portion of the hip joint formed by the pelvis. Preformed, metallic implants for bridging an acetabular bone defect, especially revision meshes, are for example NOVIOMAGUS™ brand revision meshes sold by Spierings or X-CHANGE® brand revision meshes sold by Stryker.

Flexible mesh structures are known as 3D printed textile fabrics (cellular textiles) and mesostructured cellular materials.

NOVIOMAGUS™ brand revision meshes are designed for bone graft containment when performing impaction bone grafting to restore the anatomical shape and dimensions during hip revision surgery. These sterile stainless steel implants have an anatomical shape to ensure proper fit to the acetabulum or proximal femur. Although these implants are designed to conform to the general human anatomy, they can be easily adapted to the individual patient. Such adaptation is simply provided by cutting slots at strategic positions.

Furthermore, the application WO 2015 91 518 A1 discloses a titanium mesh for revision used to repair a bone defect in knee replacement surgery. The titanium mesh for revision has transverse ribbed straps for implanting the titanium mesh for revision in a human body and longitudinal ribbed straps for supporting the transverse ribbed straps. The cross rib straps and the longitudinal rib straps are crossed and combined to form a mesh-shaped titanium mesh for revision.

Furthermore, the application EP 0 89 883 A2 discloses a mesh for bridging a gap in a bone, which is made of a biocompatible material and has a structure consisting of several mesh points at the end of arch-shaped cords. Each of its openings, which has a diameter of less than 1 mm, can accommodate a splint, and the openings allow bone screws to be removed.

Furthermore, the application US 2018/271 572 A1 describes a miniature and microscale conformal chain mail device for skeletal fixation, stabilization, and repair, and methods of making and using them. The structural devices include a conformable sheet of interconnected polygonal link elements forming a chain mesh having a first outer surface and a second outer surface. In this regard, the interconnected link elements comprise planar surfaces that combine to form the first and second outer surfaces of the conformable sheet, respectively. Also provided are methods of using the structural device to stabilize bone tissue, to fix bone tissue, as a bone graft patch, or as a thin bone tissue substitute.

The disadvantage of the application described above is that there is no mechanical stability from a defined curvature and all link elements are formed in the same way.

Thus, current solutions for the treatment of bone defects offer either a malleable mass, a completely rigid scaffold/revision mesh, or a flexible mesh structure without mechanical stability for bridging a bone defect.

SUMMARY

The present invention is therefore based on the object of providing a medical product for the treatment of bone defects, which are adaptable, flexible and yet inherently rigid scaffolds/revision meshes, in particular to improve the disadvantages of the prior art.

The object of the invention is solved in that individual link elements of the chain net are divided into connection link elements and main link elements. The connection link elements are formed differently from the main link elements, whereby the connection link elements and the main link elements form a planar grid structure in the x-y plane when linked together.

The linking of the individual link elements offers the possibility of forming a planar grid/net, which can be used for bridging a bone defect in a planar manner. The main link elements and the connection link elements of different design are per se linked to each other, in particular in an interconnected manner, by a loose connection in order to form the planar grid structure and they are movable relative to each other, preferably to a limited extent.

The advantage of the interlinked individual link elements forming a planar implant in the application to bridge bone defects is that this bridging can be used in isolation as a scaffold for bone growth or as a border for bone defect fillings.

An advantageous aspect of the present invention is that the connection link elements and the main link elements are formed three-dimensionally, or only the main link elements are formed three-dimensionally and the connection link elements are formed two-dimensionally.

By using at least two-dimensional individual link elements, different combination possibilities between main link elements and connection link elements are given, which can have different flexibility or adaptability.

It is also preferred if the planar grid structure can be curved in the z-direction and the main link elements are asymmetrical in the z-direction. In particular, the planar grid structure can be curved in the z-direction due to the loose connection of the individual link elements.

It is advantageous if the main link elements predefine a maximum curvature of the planar grid structure by their mutual contact. For adapting the scaffold, the surface formed in the x-y plane according to the first aspect can be curved in both the positive and negative z-directions. The asymmetric design of the main link elements in the z-direction provides further possibilities, as described below.

An advantageous aspect of the present invention is that the connection link elements prevent further movement of the main link elements, in particular removal from each other, when the predefined maximum curvature is reached. Thus, the medical product is limited in deformability, in particular due to the structure built from individual link elements.

In other words, the planar grid/mesh lying in the x-y plane is curved in the z-direction. As soon as a certain/predefined curvature is reached, the main link elements touch each other and prevent further curving of the grid structure. If this case has occurred, the main link elements cannot move away from each other due to the connection link elements. Thus, an interaction of the main link elements and the connection link elements ensures a rigid grid structure as soon as a maximum curvature corresponding to the predefined curvature is reached. These advantages allow the implant to adapt to the bone and still bridge a bone defect in a mechanically stable way. Before reaching the predefined and desired curvature, the scaffold provides a flexible grid structure ideally designed for adaptation which then stiffens.

In other words, the advantage here is that adaptation to the bone is made possible in such a way that the implant is flexible up to a certain curvature and is stiffened and mechanically loadable as soon as a predefined, in particular adjustable, curvature is exceeded.

Furthermore, with the help of differently shaped main link elements in combination with differently shaped connection link elements, the present solution offers the possibility of defining or setting different maximum curvatures.

It is further preferred if the predefined maximum curvature in the positive z-direction is different from the predefined maximum curvature in the negative z-direction.

This is made possible by the asymmetrical design of the main link elements in the z-direction. Thus, the planar grid structure can be brought into two different maximum curvatures and is thus defined/set differently on one side than on the other side. The asymmetry of the main link elements in the z-direction only offers a different degree of freedom of movement of the entire individual link element combination, whereby the radius of curvature is fixed.

For example, when treating an acetabular defect, a maximum radius of curvature in the positive z-direction of 20 to 30 mm is used and in the negative z-direction the maximum radius of curvature is 30 to 45 mm. Accordingly, a relative difference in the radius of curvature in the positive z-direction is 20% less than in the negative z-direction.

In the application example of the scaffold in the fitting of a skull plate defect, the maximum radius of curvature in the positive z-direction is 60 to 60 mm and the maximum radius of curvature in the negative z-direction is 60 to 90 mm. Accordingly, the relative radius of curvature in the positive z-direction is 9% less than in the negative z-direction.

It is advantageous if the main link elements and the connection link elements have a self-contained shape. Furthermore, each main link element and each connection link element has at least one opening or a hole/recess, which is defined by a closed border. In addition, it is advantageous if all main link elements and connection link elements have rounded edges and possible tips are flattened, so that also the edge of the planar grid structure has no potential for injury to the surroundings, in particular tissue. Furthermore, it is self-explanatory that such an implant can have a fastening device with which the scaffold can be fastened to a bone.

According to a first embodiment, it is advantageous if the main link elements are each formed as a framework-shaped, triangular frustum of a pyramid and the connection link elements are each formed as an eyelet-shaped polygon, in particular hexagon. According to this embodiment, one main link element has contact with three connection link elements, and one connection link element holds six main link elements together, with a side edge of each triangular frustum of a pyramid pointing toward the center of the connection link element.

According to a second embodiment, it is preferred if the main link elements are formed as framework-like, preferably elongated, quadrangular pyramids and the connection link elements are formed as a dome-shaped grid shell with at least four arched elements at the base and with correspondingly at least four (face-shaped) recesses, which are each arranged centrally between two adjacent arched elements and a lower edge of the recess is located at the level of the apex of the arched elements.

According to a third embodiment, it is advantageous if the main link elements each have a first base element formed as an eyelet-shaped polygon, in particular a hexagon, which defines a plane, and a second base element formed as an eyelet-shaped polygon, in particular a hexagon, which extends over at least one plane, which are connected to each other at the corners via orthogonal side edges, in particular of different lengths, and the connection link elements are formed by at least three arched elements connected to each other at the base in each case.

In other words, in this preferred case, the main link element consists of a framework-like polygonal/hexagonal tube whose end/front surfaces are tipped together.

According to a fourth embodiment, it is preferred if the main link elements are each formed by a connection of a first and a second central point facing each other and are connected (crown-like) with at least four side edges which are curved/arched outwards, in particular with at least two adjacent side edges having a larger bulge closer to the first central point and with at least two further adjacent side edges having a larger bulge closer to the second central point (thus assuming the basic shape of a US football) and the connection link elements are each formed as two framework-like, closed, square pyramids, which are connected to each other at their lower/bottom side to form a closed body.

When the medical product is curved according to one of the embodiments described above in the positive z-direction, i.e. in the direction of the upper side of the medical product, the distance between the edges/borders of the adjacent main link elements defining the upper side of the main link elements becomes larger and the distance between the edges/borders of the adjacent main link elements defining the lower side of the main link elements becomes smaller. As soon as the edges of the main link elements that define the lower side of the main link elements touch, the maximum predefined curvature is reached and the medical product stiffens, or the main link elements and connection link elements become interlocked such that no further movement is possible.

When the medical product is curved according to one of the embodiments described above in the negative z-direction, i.e. in the direction of the lower side of the medical product, the distance between the edges/borders of the adjacent main link elements defining the lower side of the main link elements becomes larger and the distance between the edges/borders of the adjacent main link elements defining the upper side of the main link elements becomes smaller. As soon as the edges of the main link elements that define the upper side of the main link elements touch, the maximum predefined curvature is reached and the medical product stiffens, or the main link elements and connection link elements become interlocked such that no further movement is possible.

BRIEF DESCRIPTION OF THE DRAWING FIGURES

DETAILED DESCRIPTION

Examples of embodiments of the present disclosure are described below on the basis of the accompanying figures. The figures are merely schematic in nature and are intended to aid in understanding the invention. Identical elements are designated by the same reference signs.

First Embodiment

Figure 1:
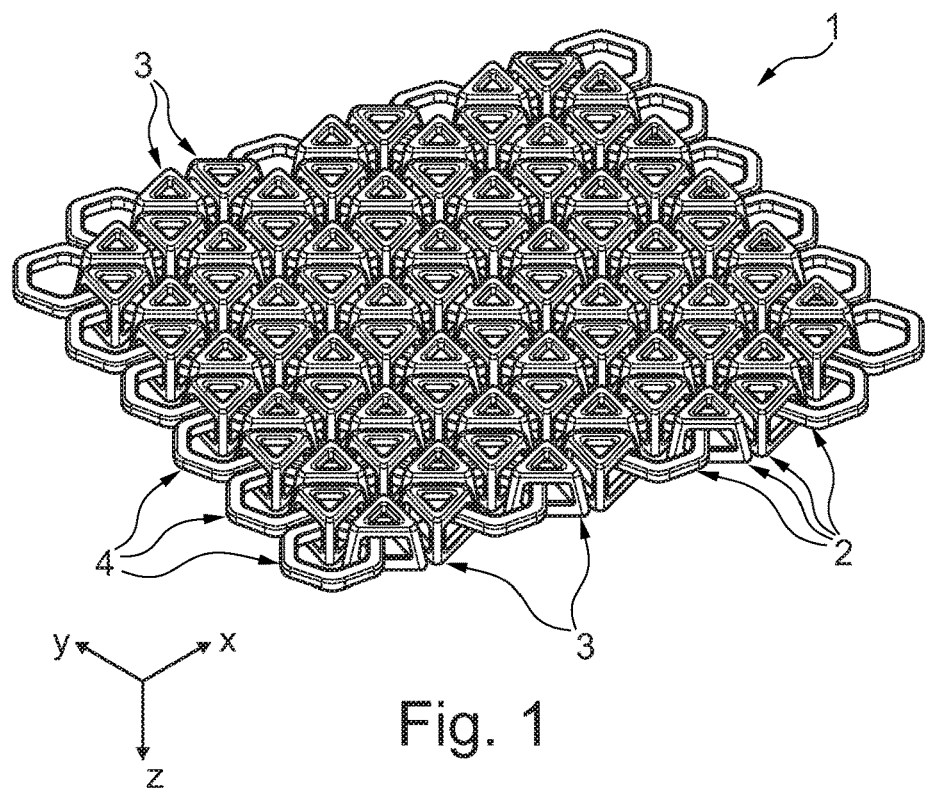
FIG. 1 is a representation of the medical product according to a first embodiment of the present disclosure.

FIG. 1 is a representation of the medical product 1 according to a first embodiment. The shown medical product 1 shows a plurality of individual link elements 2, which are connected to each other in such a way that adjacent individual link elements 2 are interlinked. The individual link elements 2 can be subdivided/split into main link elements 3 and connection link elements 4, which have a different geometry/shape with respect each other.

The interlinking of the individual link elements 2 and the main link elements 3 and the connection link elements 4 shown in FIG. 1 creates a planar grid structure that lies in the x-y plane and can be bent in the z-direction.

Figure 2:
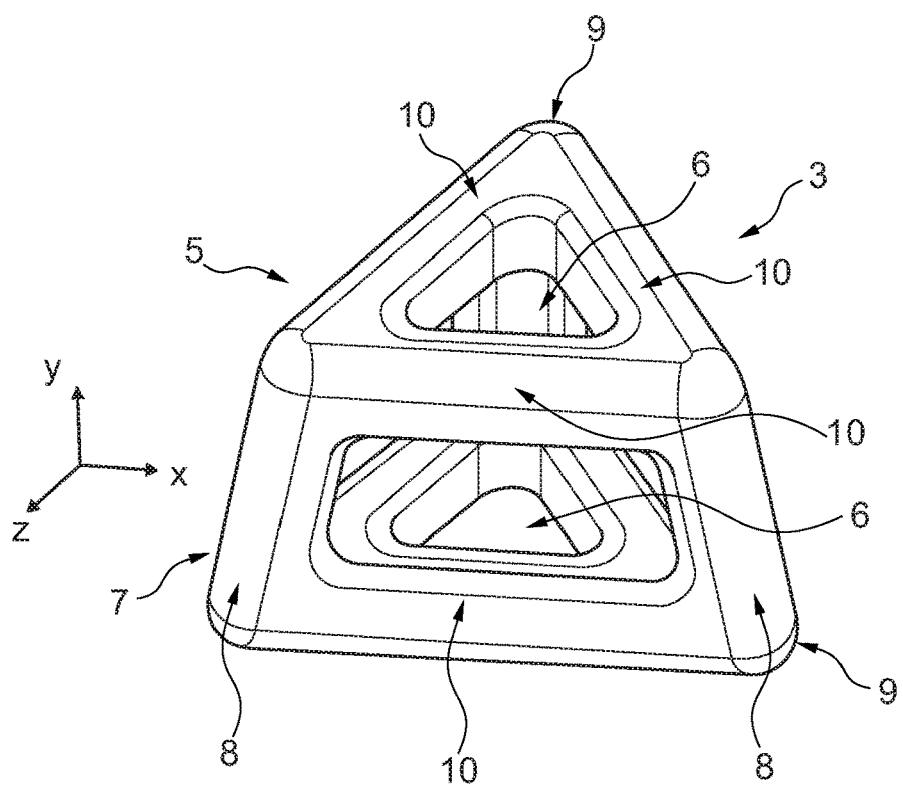
FIG. 2 is a representation illustrating a three-dimensional main link element according to the first embodiment of the present disclosure.

In FIG. 2, it can be seen that a main link element 3 has a triangular shape in plan view, in particular the shape of an equilateral triangle. A base edge 10 of a first main link element 3 is adjacent to a base edge 10 of a second main link element 3. When the main link elements 3 are joined together in this manner, six main link elements 3 are each connected to each other by a connection link element 4, provided that the connection link element 4 is located in the center of the medical product 1, in particular of the implant. A main link element 3 located in the center of the medical product 1 is in contact with three connection link elements 4.

FIG. 2 is a representation illustrating a three-dimensional main link element 3 according to the first embodiment of the present disclosure. The main link element 3 of the first embodiment is a framework-like, triangular frustum of a pyramid. In other words, the main link element 3 has a first three-dimensional triangle 5 with a first triangular recess 6 at its center and a second three-dimensional triangle 7 with a second triangular recess 6 at its center. The first triangle 5 is arranged above the second triangle 7 and the base area of the first triangle 5 is smaller than the base area of the second triangle 7. The tips 9 of the two triangles 5 and 7 are connected to each other via the three side edges 8 of the frustum of a pyramid with an angle of inclination adapted to the different base areas.

The edges and corners of the main link element 3 shown in FIG. 2 as a framework-like, triangular frustum of a pyramid are rounded. The main link element 3 according to the first embodiment is asymmetric in the z-direction, since the lower triangle 7 is larger than the upper triangle 5, and is only symmetric in the y-axis direction. In particular, the angles of inclination of the three side edges 8 can be the same or different according to each other, which also affects the symmetry ratios.

Figure 3:
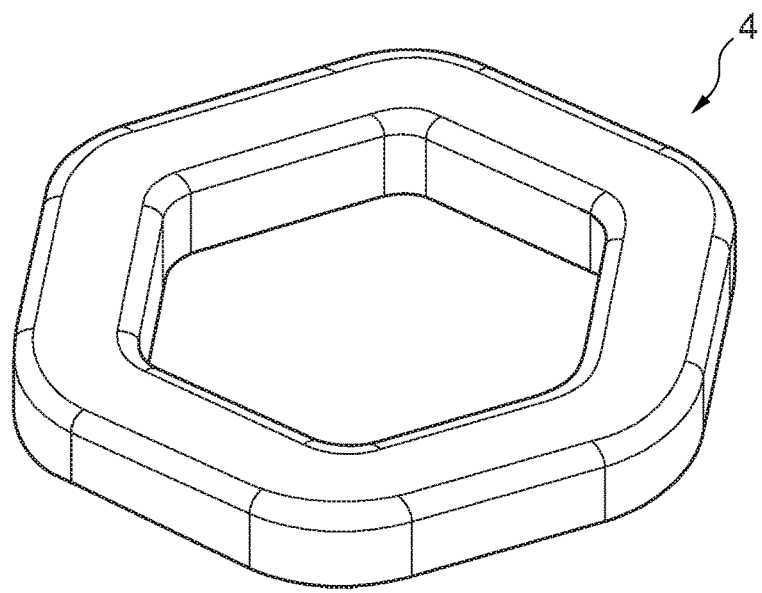
FIG. 3 is a representation illustrating a two-dimensional connection link element according to the first embodiment of the present disclosure.

FIG. 3 is a representation illustrating a two-dimensional connection link element 4 according to the first embodiment of the present disclosure. The connection link element 4 of the first embodiment is exemplarily formed as an eyelet-shaped hexagon.

The connection link element 4 also has rounded edges and corners. The eyelet-shaped hexagon has a uniform thickness over the entire circumference. The connection link element 4 according to the first embodiment is symmetric in the x-, y- and z-axis direction as well as point symmetric.

Figure 4:
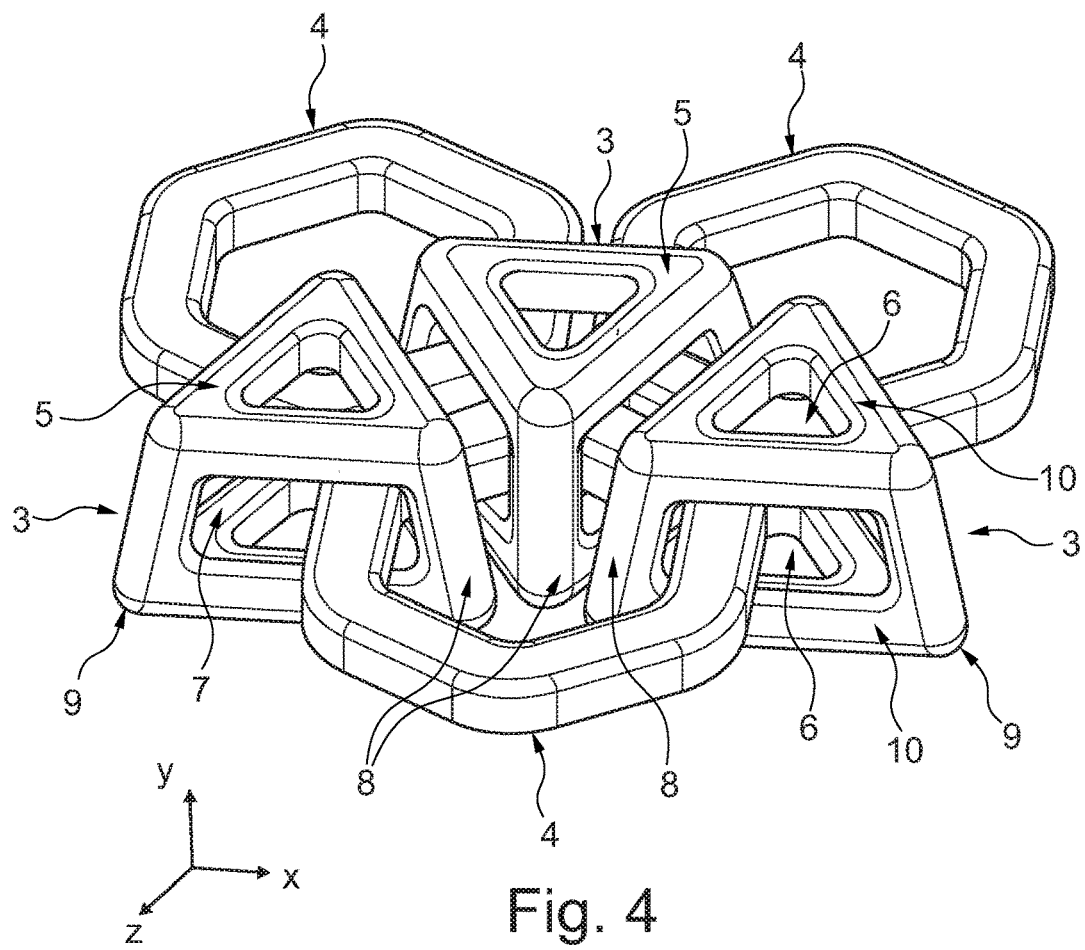
FIG. 4 is a sectional view of the medical product according to the first embodiment of the present disclosure.

FIG. 4 is a sectional view of the medical product 1 according to the first embodiment. It can be seen that a main link element 3 is in contact with three connection link elements 4. One corner of the eyelet-shaped hexagon shown is used to hold a side edge 8 of the frustum of a pyramid. In the partial view, it is shown that due to the shape of the frustum of a pyramid, the distance between the base sides of two adjacent second triangles 7 is less than the distance between the base sides of two adjacent first triangles 5.

When the medical product 1 is curved according to the first embodiments described above in the positive z-direction, i.e. in the case where the curvature of the implant points towards the upper side of the frustum of a pyramid, the distance between the base edges of the adjacent triangles 5 defining the respective upper side of the frusta of pyramids increases and the distance between the base edges of the adjacent triangles 7 defining the respective lower side of the frusta of pyramids decreases. As soon as the base edges of the triangles 5, which define the respective lower side of the frusta of pyramids, touch, the maximum predefined curvature is reached and the medical product 1 stiffens, or the main link elements 3 and connection link elements 4 interlock with each other in such a way that no further movement is possible.

When the medical product 1 is curved according to the first embodiments described above in the negative z-direction, i.e. in the case where the curvature of the implant points towards the lower side of the frustum of a pyramid, the distance between the base edges of the adjacent triangles 5 defining the respective upper side of the frusta of pyramids becomes smaller and the distance between the base edges of the adjacent triangles 7 defining the respective lower side of the frusta of pyramids becomes larger. As soon as the base edges of the triangles 7 that define the respective upper side of the frusta of pyramids touch, the maximum predefined curvature is reached and the medical product 1 stiffens, or the main link elements 3 and connection link elements 4 interlock with each other in such a way that no further movement is possible.

Figure 5:
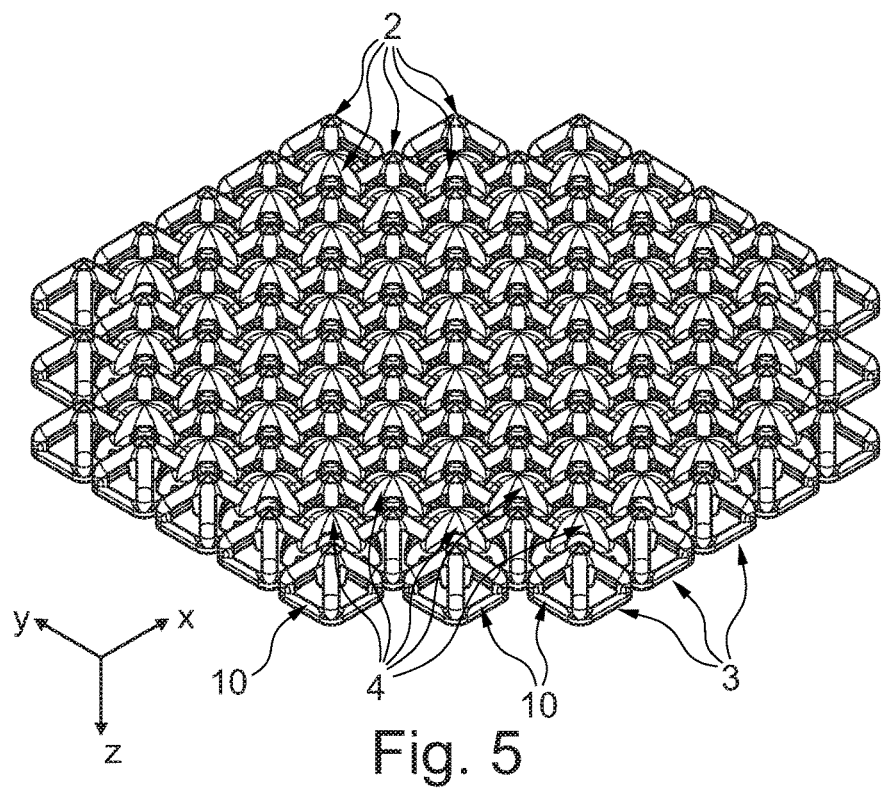
FIG. 5 is a representation of the medical product according to a second embodiment of the present disclosure.

FIG. 5 is a representation of the medical product 1 according to a second embodiment. The medical product 1 shown has a large number of individual link elements 2, which are connected to each other in such a way that adjacent individual link elements 2 are interlinked. As in the first embodiment, these individual link elements 2 are also divided into main link elements 3 and connection link elements 4, which have a different geometry/shape with respect to each other.

The interlinking of the individual link elements 2 or respectively of the main link elements 3 and the connection link elements 4 shown in FIG. 5 creates a planar grid structure that lies in the x-y plane and can be curved/bent in the z-direction.

In FIG. 5, it can be seen that a main link element 3 has a four-sided pyramid shape in plan view. Furthermore, the pyramid tip 9 with the side edges 8 can be seen and the side edges 8 end in the corners of a quadrangular base area. A view from below shows tetragons arranged in a row corresponding to the base area of the main link element 3. A base edge 10 of a first main link element 3 is adjacent to a base edge 10 of a second main link element 3. In such joining of the main link elements 3, four main link elements 3 are each connected to each other by a connection link element 4, provided that the connection link element 4 is located in the center of the medical product 1, in particular of the implant. A main link element 3, which is located in the center of the medical product 1, is in contact with four connection link elements 4. The formation of the arched elements 11 on the connection link elements 4 serves to overlap a respective base edge 10 of the adjacent/neighboring main link element.

The edge of the medical product of the second embodiment is preferably formed by main link elements 3.

Figure 6:
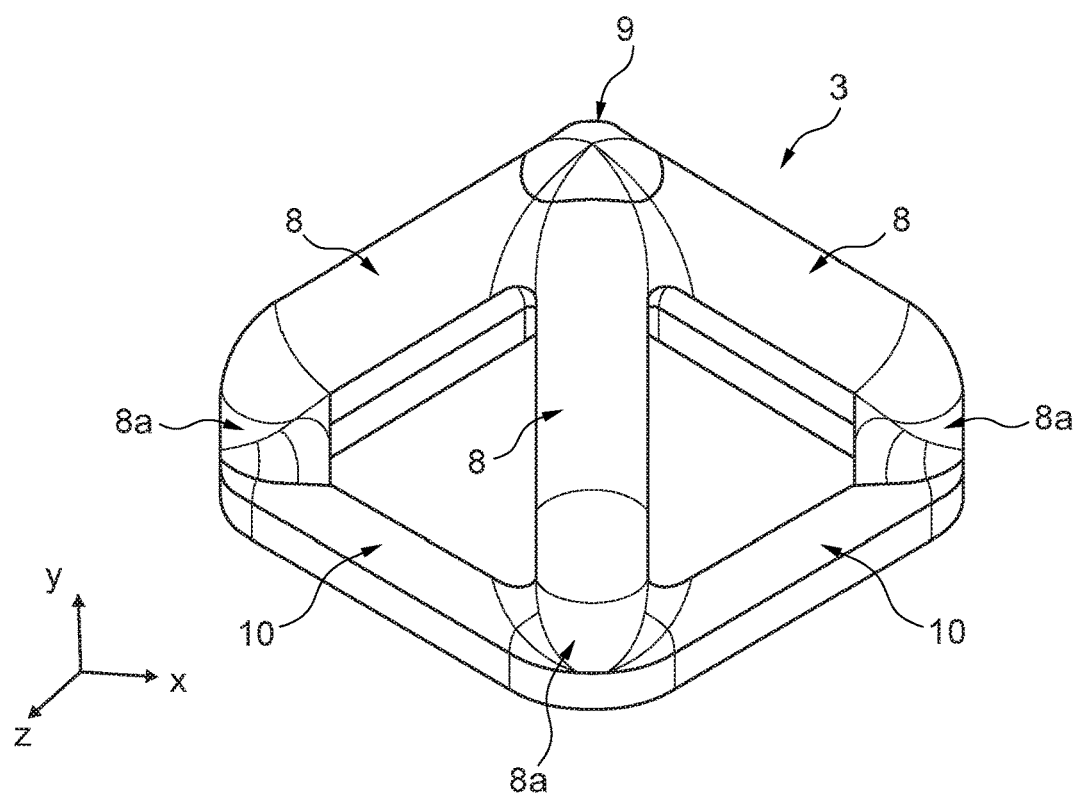
FIG. 6 is a representation illustrating a three-dimensional main link element according to the second embodiment of the present disclosure.

FIG. 6 is a representation illustrating a three-dimensional main link element 3 according to the second embodiment of the present disclosure. The main link element 3 of the second embodiment is formed as a framework-like, elongated, quadrangular pyramid, hereinafter referred to as an enneahedron. In other words, it is a framework-like, quadrangular pyramid, wherein the four side edges 8 of the framework-like pyramid terminate in the corners of the quadrangular base area via a respective side edge 8a perpendicular to the bottom/lower side. The square base area is also framework-like and forms the four base edges 10.

Figure 7:
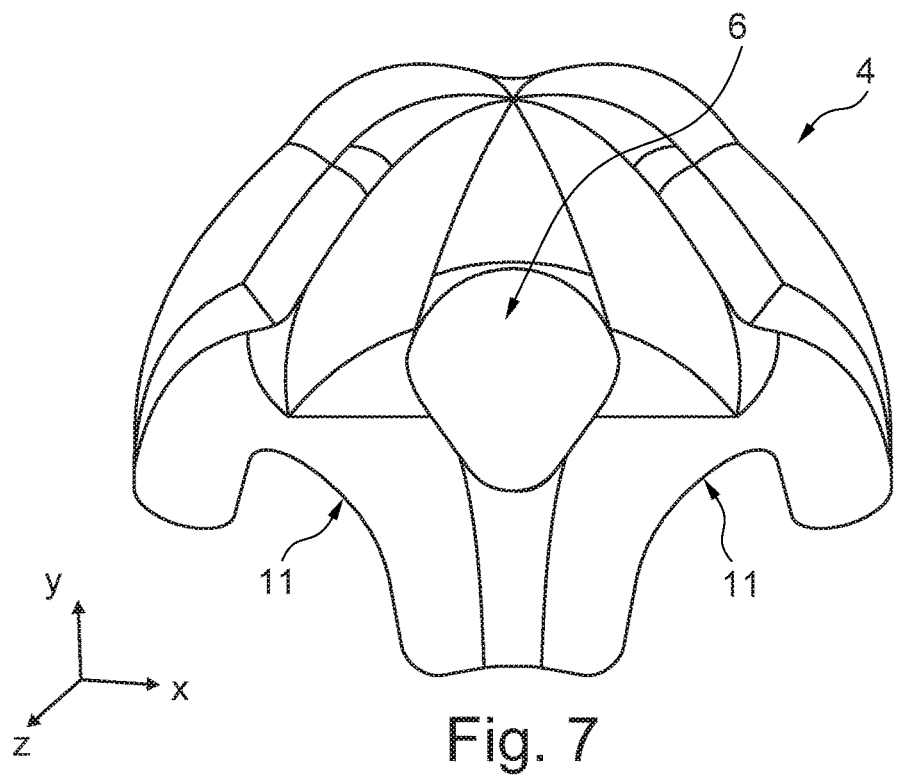
FIG. 7 is a representation illustrating a three-dimensional connection link element according to the second embodiment of the present disclosure.
Figure 8:
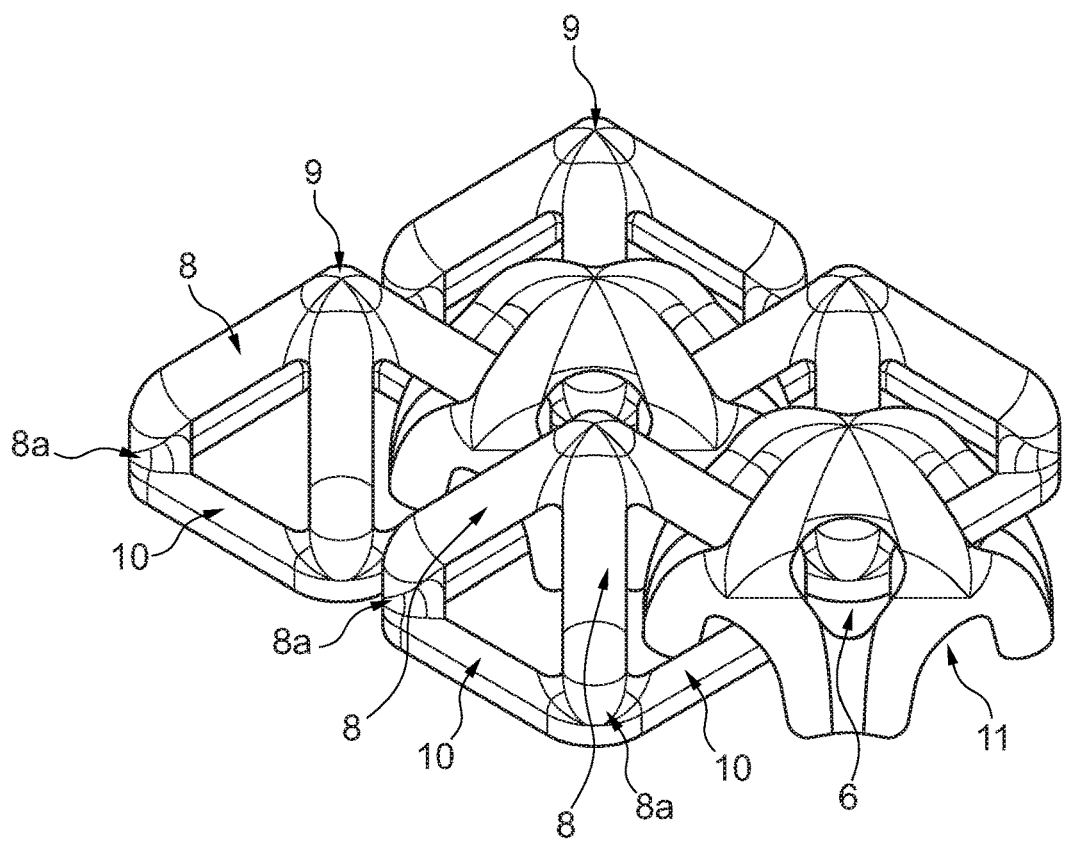
FIG. 8 is a sectional view of the medical product according to the second embodiment of the present disclosure.

FIG. 7 is a representation illustrating a connection link element 4 according to the second embodiment of the present disclosure. The connection link element 4 is in the form of a dome-shaped grid shell with at least four arched elements 11 at the base and correspondingly at least four oval, in particular face-shaped, recesses 6 in each case centrally between two adjacent arched elements 11, the lower edge of the recess 6 lying at the level of the apex of the arched elements 11.

In other words, the connection link element 4 of the second embodiment has a similar structure of a cross-ribbed dome with four arched elements 11 at the base, which each have an oval, in particular face-shaped, recess 6 as described above. This structure is also similar in shape and structure to a pavilion tent with four legs.

The edges and corners, as well as the tip 9 of the framework-like enneahedron of the main link element 3 shown in FIG. 6 and of the connection link element 4 shown in FIG. 7 are rounded. The main link element 3 according to the second embodiment is asymmetric in the z-direction and is only symmetric in the y-axis direction. The connection link element 3 is rotationally symmetrical and has symmetry starting from the x-axis and y-axis.

FIG. 6 is a partial view of the medical product 1 according to the second embodiment. It can be seen that a main link element 3 is in contact with four connection link elements 4. A side edge 8 of the main link element 3 shown passes through a recess 6 of the connection link element 4 in contact therewith. The arched elements 11 of the connection link element 4 serve to overlap a base edge 10 of the enneahedron.

When the medical product 1 is curved according to the first embodiments described above in the positive z-direction, i.e. in the case the curvature points in the direction of the upper side of the enneahedron, the distance between the side edges 8 of the adjacent enneahedra defining the respective upper side of the enneahedron increases and the distance between the base edges 10 of the adjacent triangles 7 defining the respective lower side of the enneahedron decreases. As soon as the base edges 8, which define the respective lower side of the enneahedron, touch, the maximum, predefined curvature is reached and the medical product 1 stiffens, or the main link elements 3 and connection link elements 4 interlock with each other such that no further movement is possible.

When the medical product 1 is curved according to the first embodiments described above in the negative z-direction, i.e. in the case the curvature points towards the lower side of the enneahedron, the distance between the side edges 8 of the enneahedron defining the respective upper side of the frusta of pyramids becomes smaller and the distance between the base edges 10 of the enneahedron defining the respective lower side of the enneahedron becomes larger. As soon as the side edges 8 of the enneahedron, which define the respective upper side of the enneahedron, touch, the maximum predefined curvature is reached and the medical product 1 stiffens, or the main link elements 3 and connection link elements 4 interlock with each other in such a way that no further movement is possible.

Figure 9:
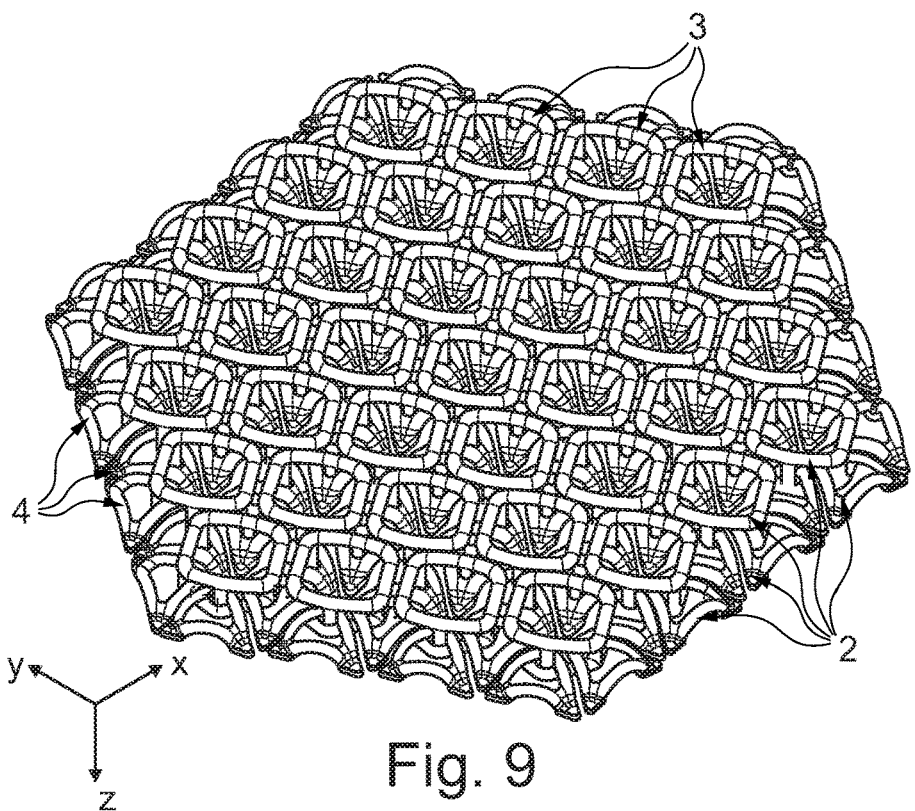
FIG. 9 is a representation of the medical product according to a third embodiment of the present disclosure.

FIG. 9 is a representation of the medical product 1 according to a third embodiment. FIG. 9 is a representation of the medical product 1 according to a third embodiment. The shown medical product 1 shows a plurality of individual link elements 2, which are interconnected in such a way that individual link elements 2 adjacent to each other are interlinked. As in the first and second embodiment, these individual link elements 2 are also subdivided/split into main link elements 3 and connection link elements 4, which have a different geometry/shape with respect to each other.

The interlinking of the individual elements 2 or respectively the main link elements 3 and the connection link elements 4 shown in FIG. 9 creates a planar grid structure that lies in the x-y plane and can be curved/bent in the z-direction.

FIG. 9 shows that a main link element 3 is an irregular hexagon in plan view. The base edges 10 of the hexagonal base area of a main link element 3 face the base edges 10 of the adjacent main link element 3. In such joining of the main link elements 3, a main link element 3 is interconnected to six connection link elements 4, respectively, provided that the connection link element 4 is located in the center of the medical product 1, in particular of the implant. A connection link element 4 located in the center of the medical product 1 is in contact with three main link elements 3.

The edge of the medical product according to the second embodiment is preferably formed by connection link elements 4.

Figure 10:
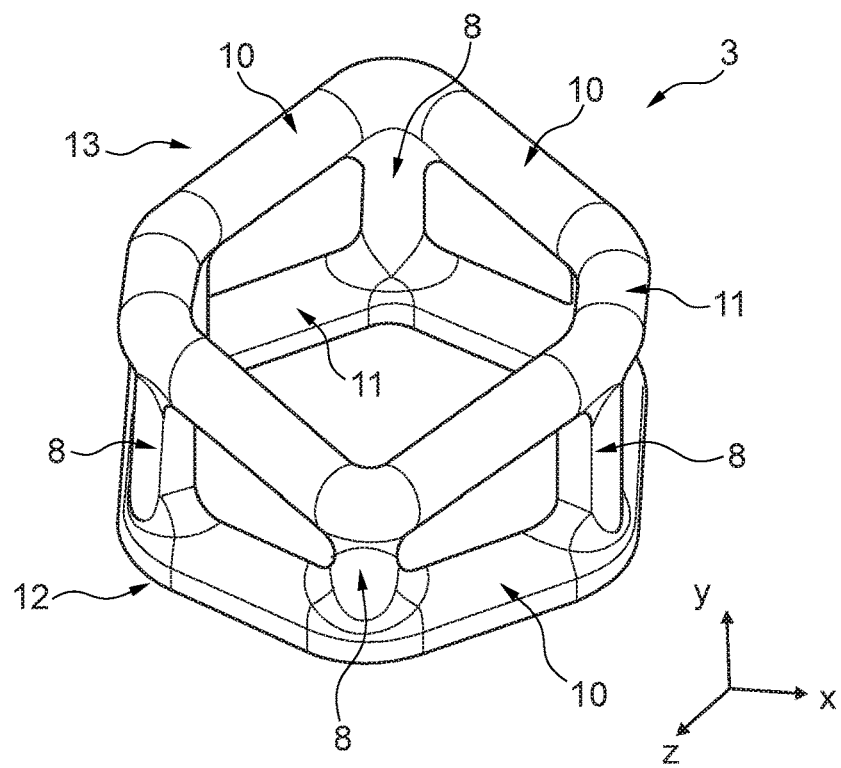
FIG. 10 is a representation illustrating a three-dimensional main link element according to the third embodiment of the present disclosure.

FIG. 10 is a representation illustrating a three-dimensional main link element 3 according to the third embodiment of the present disclosure. The main link element 3 has in each case a first base element 12 formed as an eyelet-shaped polygon, in particular a hexagon, which lies in a plane, and a second base element 13 formed as an eyelet-shaped polygon, in particular a hexagon, which extends over at least one plane. At the corners, the two base elements 12 and 13 are connected to each other via orthogonal side edges 8, in particular of different lengths, the base element 13 being the upper base element.

In other words, the third embodiment is two hexagons arranged one above the other, which are connected to each other with side edges 8 of different heights/lengths, and the side edges 8 are perpendicular to the lower base element 12. The upper base element 13 is adapted to the side edges 8 of different heights and therefore extends over several levels, in particular three levels.

According to the representation in FIG. 10, it is preferred if the shortest side edge 8 is arranged opposite the longest side edge 8 and the four remaining side edges 8 are of the same design, but smaller than the longest side edge 8 and longer than the shortest side edge 8.

Figure 11:
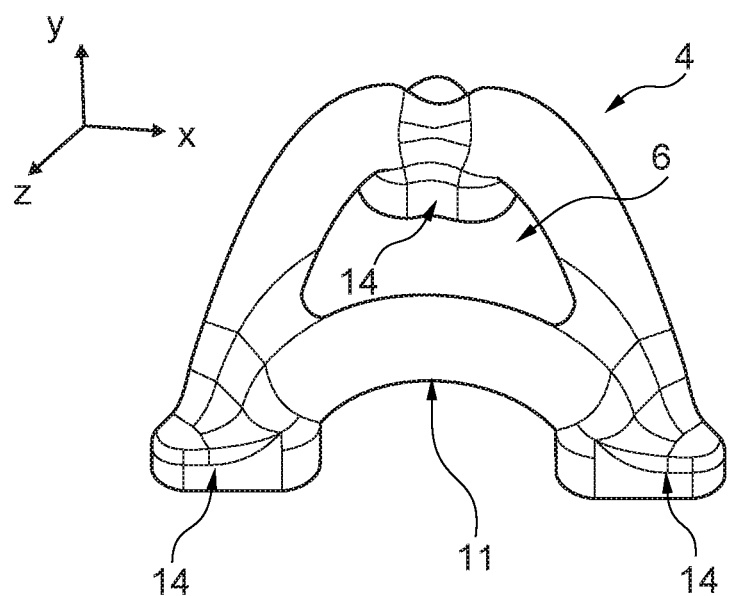
FIG. 11 is a representation illustrating a three-dimensional connection link element according to the third embodiment of the present disclosure.

FIG. 11 is a representation illustrating a three-dimensional connection link element 4 according to the third embodiment of the present disclosure. The connection link element 4 is formed by at least three arched elements 11 interconnected at the base. The interconnected arched elements 11 form an opening in the upward direction (positive z-direction), which is hereinafter referred to as recess 6. The interconnected bases of the three arched elements 11 each form a support leg 14. The at least three support legs 14 span a triangular base area and have a foot-like formation towards the outside.

The edges and corners are rounded, as shown in FIGS. 10 and 11. The main link element 3 is asymmetrical in the z-direction.

Figure 12:
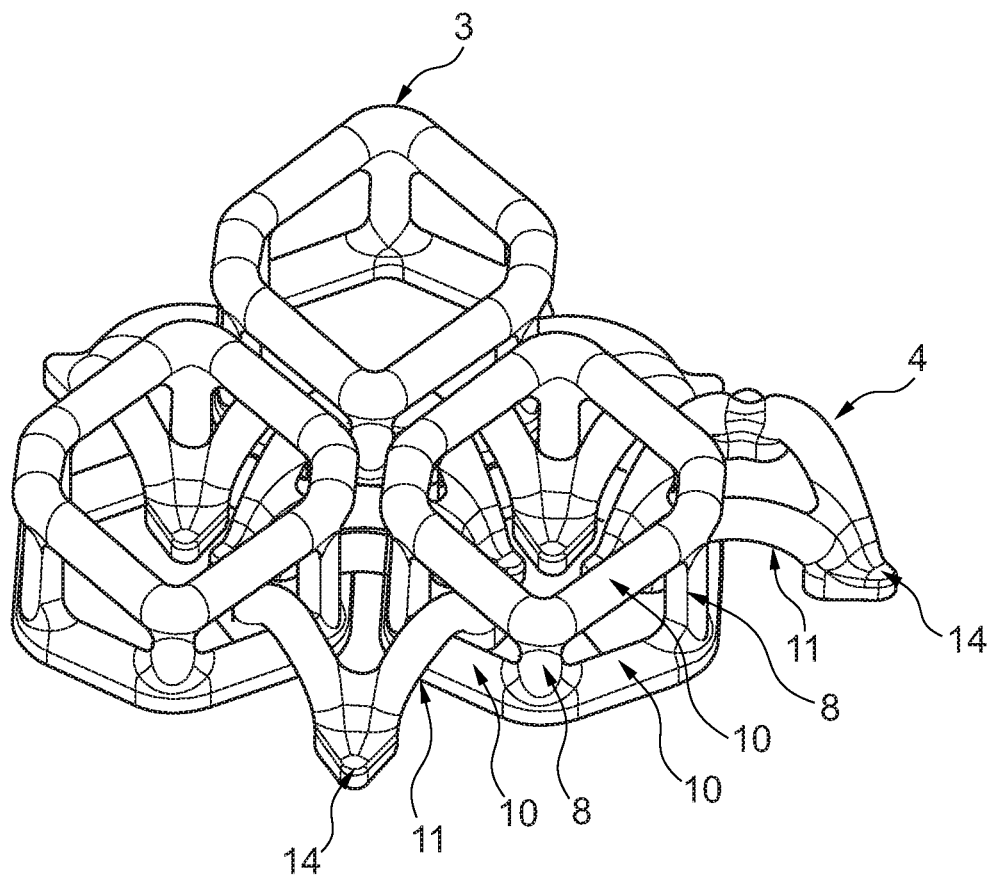
FIG. 12 is a sectional view of the medical product according to the third embodiment of the present disclosure.

FIG. 12 is a sectional view of the medical product 1 according to the third embodiment. It can be seen that a main link element 3 is in contact with six connection link elements 4. Each side edge 8 of the main link element 3 shown is embraced by a connection link element 4 in contact therewith. The arched elements 11 of the connection link element 4 serve to reach over a base edge 10 of the main link element 3. In other words, the recess 6 of a connection link element 4 reaches around a side edge 8 of each of the three adjacent main link elements 3.

When the medical product 1 is curved according to the third embodiment described above in the positive z-direction, i.e. in the case where the curvature points in the direction of the upper base element 13 of the main link element 3, the distance between the base edges 10 of the adjacent hexagons defining the respective upper base element 13 of the main link element 3 becomes larger and the distance between the base edges 10 of the adjacent hexagons defining the respective lower base element 12 becomes smaller. As soon as the base edges 10 of the hexagons that define the respective lower base element 12 touch, the maximum predefined curvature is reached and the medical product 1 stiffens, or the main link elements 3 and connection link elements 4 interlock with each other in such a way that no further movement is possible.

When the medical product 1 is curved according to the first embodiments described above in the negative z-direction, i.e. in the case where the curvature points in the direction of the lower base element 12 of the main link element 3, the distance between the base edges 10 of the adjacent hexagons defining the respective lower base element 12 of the main link element 3 becomes smaller and the distance between the base edges 10 of the adjacent hexagons defining the respective lower base element 12 of the main link element 3 becomes larger. As soon as the base edges 10 of the hexagons defining the respective upper base element 13 of the main link element 3 touch, the maximum predefined curvature is reached and the medical product 1 stiffens, or the main link elements 3 and connection link elements 4 interlock with each other in such a way that no further movement is possible.

Figure 13:
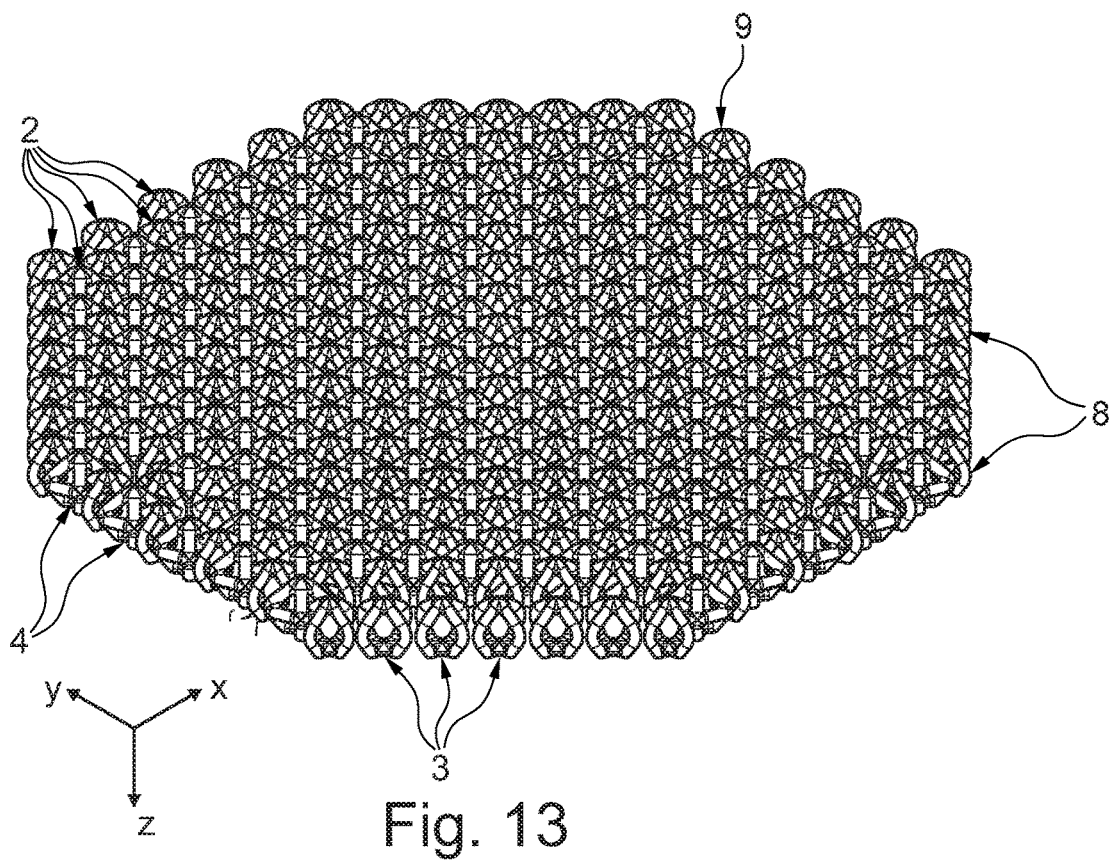
FIG. 13 is a representation of the medical product according to a fourth embodiment of the present disclosure.

FIG. 13 is an embodiment of the medical product 1 according to a fourth embodiment. FIG. 13 is a partial representation of the medical product 1 according to the fourth embodiment. The shown medical product 1 shows a plurality of individual link elements 2, which are interconnected in such a way that individual link elements 2 adjacent to each other are interlinked. According to the first and second embodiment, the individual link elements 2 are subdivided/split into main link elements 3 and connection link elements 4, which have a different geometry/shape with respect to each other.

The interlinking of the individual link elements 2 or respectively of the main link elements 3 and the connection link elements 4 shown in FIG. 13 creates a planar grid structure that lies in the x-y plane and can be bent in the z-direction.

In FIG. 13, the top view shows only pyramid-like tips 9, from which side edges 8 lead into the planar grid structure. If the medical product is viewed from the lower side, the same picture can be seen.

Figure 14:
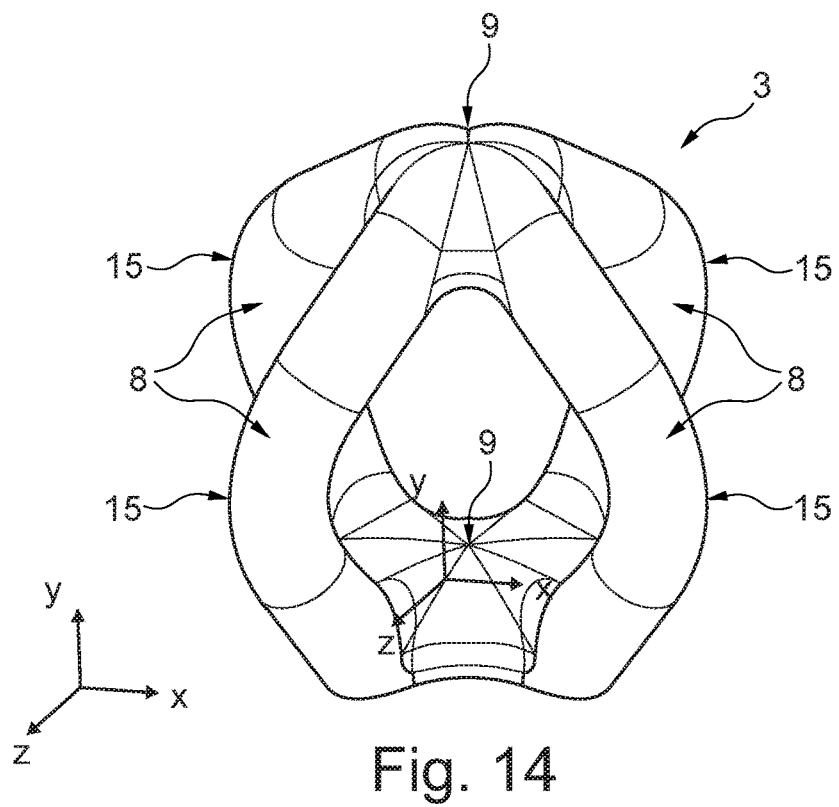
FIG. 14 is a representation illustrating a three-dimensional main link element according to the fourth embodiment of the present disclosure.

FIG. 14 is a representation illustrating a three-dimensional main link element 3 according to the fourth embodiment of the present disclosure. The main link element is formed by connecting a first and a second central point 9 that are opposite to each other and are connected in a crown-like manner with at least four side edges 8 which are curved/arched outwards, in particular with at least two adjacent side edges 8 having a larger bulge 15 closer to the first central point 9 and with at least two further adjacent side edges 8 having a larger bulge 15 closer to the second central point 9. Thus, the bulges 15 are preferably not located in the center of the curved/arched side edges 8.

Figure 15:
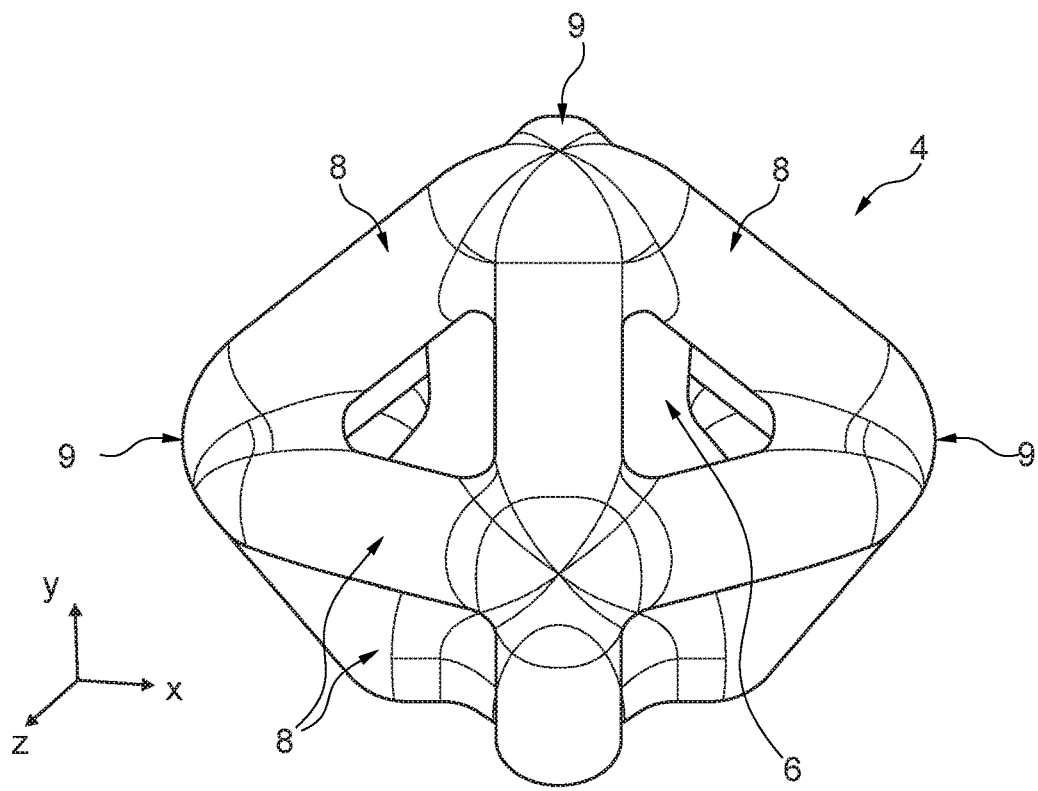
FIG. 15 is a representation illustrating a three-dimensional connection link element according to the fourth embodiment of the present disclosure.

FIG. 15 is a representation illustrating a three-dimensional connection link element 4 according to the fourth embodiment of the present disclosure. The connection link element 3 is formed by two framework-like, closed, quadrangular pyramids, which are connected to each other at the lower/bottom side to form a closed body.

In other words, the connection link element 4 of the fourth embodiment is a polyhedron formed by eight triangle faces, in particular equilateral triangle faces, with rounded corners and edges, and with a triangular recess 6 in each formed triangle face. This triangular recess 6 is preferably adapted in its shape to the triangle face. The borders of the triangular recesses 6 correspond to the side edges 8 described above. Four converging side edges 8 form a central point 9.

The corners and edges of the main link element 3 and connection link element 4 described above have rounded corners and edges. The main link element 3 according to FIG. 14 is again asymmetrical in the z-direction. The connection link element 4 as shown in FIG. 15 is symmetrical along the x, y and z axes and is also point-symmetrical.

Figure 16:
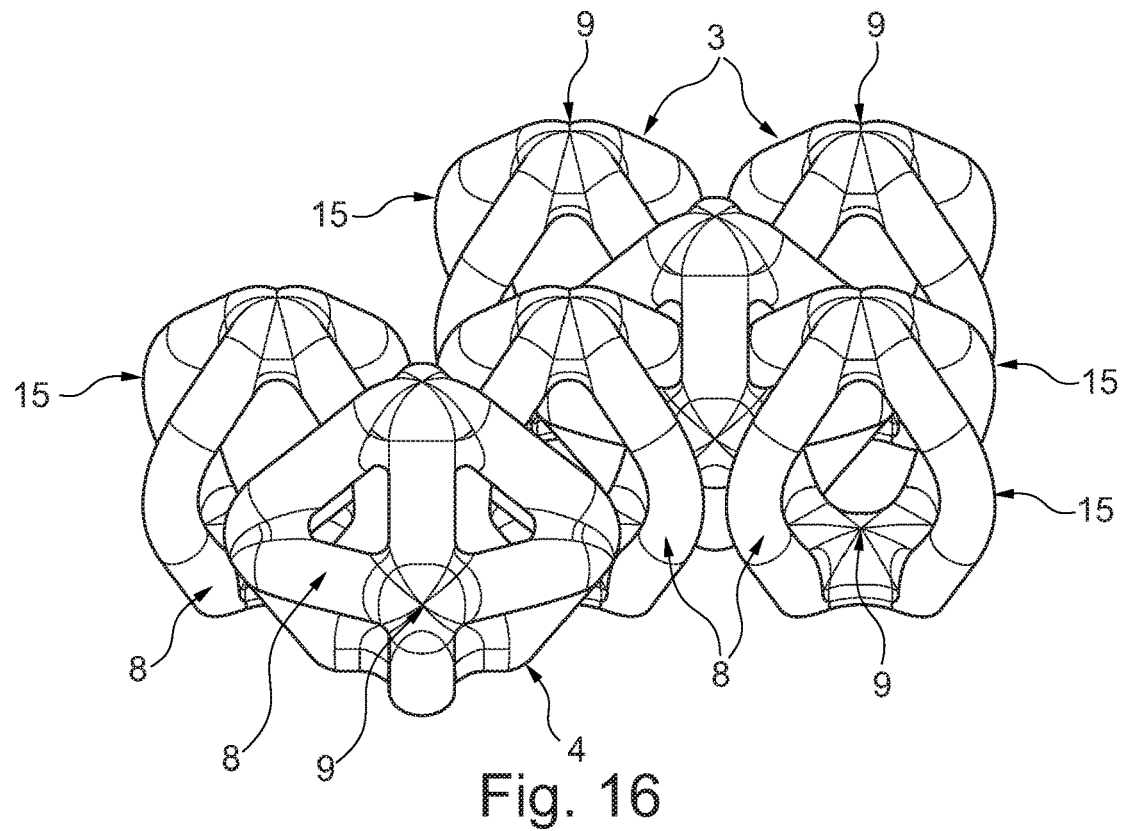
FIG. 16 is a sectional view of the medical product according to the fourth embodiment of the present disclosure.

FIG. 16 is a sectional view of the medical product 1 according to the fourth embodiment of the present disclosure. It can be seen that a main link element 3 is in contact with four connection link elements 4. Each side edge 8 of the main link element 3 shown is guided by two adjacent recesses 6, one above the other, of a connection link element 4 in contact therewith.

When the medical product 1 is curved according to the third embodiment described above in the positive z-direction, i.e. in the case the curvature points towards the upper central point 9 of the main link element 3, the distance between the curved side edges 8 defining the respective upper side of the main link element 3 becomes larger and the distance between the curved side edges 8 defining the respective lower side of the main link element 3 becomes smaller. As soon as the side edges 8 of the main link elements 3, which define the respective lower side of the main link element 3, touch, the maximum, predefined curvature is reached and the medical product 1 stiffens, or the main link elements 3 and connection link elements 4 interlock with each other so that no further movement is possible.

When the medical product 1 is curved according to the third embodiment described above in the negative z-direction, i.e. in the case the curvature points towards the lower central point 9 of the main link element 3, the distance between the curved side edges 8 defining the respective upper side of the main link element 3 becomes smaller and the distance between the curved side edges 8 defining the respective lower side of the main link element 3 becomes larger. As soon as the side edges 8 of the main link elements 3, which define the respective lower side of the main link element 3, touch, the maximum, predefined curvature is reached and the medical product 1 stiffens, or the main link elements 3 and connection link elements 4 interlock with each other so that no further movement is possible.

In particular, any combination of the main link elements and connection link elements described above is conceivable.

The invention claimed is:

1. A medical product for use in treating a bone defect, the medical product comprising a plurality of individual link elements which are connected to each other in such a way that adjacent individual link elements interlock/are linked to each other, the individual link elements being subdivided into main link elements and connection link elements, the connection link elements having a different geometric form than the main link elements, the main link elements and the connection link elements forming a planar grid structure which is planar in an x-y plane in an interlinked state, wherein the main link elements are formed as framework-shaped quadrangular pyramids and the connection link elements are formed as a dome-shaped grid shell, wherein the connection link elements are formed with at least four arched elements at a base and with correspondingly at least four recesses, which are each arranged centrally between two adjacent arched elements and a lower edge of each recess is located at a level of an apex of one of the arched elements.

2. The medical product according to claim 1, wherein the main link elements are asymmetrical in a z-direction.

3. The medical product according to claim 2, wherein the planar grid structure is curvable in the z-direction and the main link elements predefine a maximum curvature of the planar grid structure by their mutual contact.

4. The medical product according to claim 3, wherein the connection link elements prevent movement of the main link elements upon reaching the maximum curvature and the maximum curvature in a positive z-direction is different from the maximum curvature in a negative z-direction.

5. A medical product for use in treating a bone defect, the medical product comprising a plurality of individual link elements which are connected to each other in such a way that adjacent individual link elements interlock/are linked to each other, the individual link elements being subdivided into main link elements and connection link elements, the connection link elements having a different geometric form than the main link elements, the main link elements and the connection link elements forming a planar grid structure which is planar in an x-y plane in an interlinked state, wherein the main link elements each have a first base element formed as an eyelet-shaped polygon, which defines a first plane, and a second base element formed as an eyelet-shaped polygon, which extends over a second plane, which are connected to each other at corners via orthogonal side edges, and the connection link elements are each formed by at least three arched elements connected to each other at a base.

6. The medical product according to claim 5, wherein the main link elements are asymmetrical in a z-direction.

7. The medical product according to claim 6, wherein the planar grid structure is curvable in the z-direction and the main link elements predefine a maximum curvature of the planar grid structure by their mutual contact.

8. The medical product according to claim 7, wherein the connection link elements prevent movement of the main link elements upon reaching the maximum curvature and the maximum curvature in a positive z-direction is different from the maximum curvature in a negative z-direction.

9. A medical product for use in treating a bone defect, the medical product comprising a plurality of individual link elements which are connected to each other in such a way that adjacent individual link elements interlock/are linked to each other, the individual link elements being subdivided into main link elements and connection link elements, the connection link elements having a different geometric form than the main link elements, the main link elements and the connection link elements forming a planar grid structure which is planar in an x-y plane in an interlinked state, wherein the main link elements are each formed by a connection of a first and a second central point, which are opposite to each other and are connected with at least four side edges which are bent/curved outwards, and the connection link elements are each formed as two framework-shaped, closed, quadrangular pyramids which are connected to each other at their lower/bottom side to form a closed body.

10. The medical product according to claim 9, wherein the main link elements are asymmetrical in a z-direction.

11. The medical product according to claim 10, wherein the planar grid structure is curvable in the z-direction and/or the main link elements predefine a maximum curvature of the planar grid structure by their mutual contact.

12. The medical product according to claim 11, wherein the connection link elements prevent movement of the main link elements upon reaching the maximum curvature and the maximum curvature in a positive z-direction is different from the maximum curvature in a negative z-direction.

\* \* \* \* \*